United States Patent
Collins et al.

(10) Patent No.: US 6,541,484 B2
(45) Date of Patent: Apr. 1, 2003

(54) PYRAZOLO-PYRIDINE DERIVATIVES AS LIGANDS FOR GABA RECEPTORS

(75) Inventors: Ian James Collins, Ware (GB); Linda Elizabeth Keown, Great Dunmow (GB); Leslie Joseph Street, Little Hallingbury (GB)

(73) Assignee: Merck Sharp & Dohme Limited, Hoddesdon ( * ) Notice: Subject to any disclaimer, the term of this patent is extended or adjusted under 35 U.S.C. 154(b) by 0 days.

(21) Appl. No.: 10/149,850

(22) PCT Filed: Dec. 5, 2000

(86) PCT No.: PCT/GB00/04652

§ 371 (c)(1),
(2), (4) Date: Jun. 14, 2002

(87) PCT Pub. No.: WO01/44244

PCT Pub. Date: Jun. 21, 2001

(65) Prior Publication Data

US 2003/0004180 A1 Jan. 2, 2003

(30) Foreign Application Priority Data

Dec. 15, 1999 (GB) .............................................. 9929685

(51) Int. Cl.$^7$ .................... C07D 471/04; C07D 471/08; C07D 471/14; A61K 31/435; A61K 31/47

(52) U.S. Cl. ....................... 514/286; 514/287; 514/293; 514/303; 546/63; 546/64; 546/82; 546/119; 546/120

(58) Field of Search ................................. 546/119, 120, 546/63, 64, 82; 514/303, 286, 287, 293

(56) References Cited

FOREIGN PATENT DOCUMENTS

| WO | WO 99/00391 | 1/1999 |
|----|-------------|--------|
| WO | WO 99/06399 | 2/1999 |
| WO | WO 99/37644 | 7/1999 |
| WO | WO 99/48892 | 9/1999 |

Primary Examiner—Bernard Dentz
(74) Attorney, Agent, or Firm—J. Eric Thies; Melvin Winokur

(57) ABSTRACT

A class of substituted and/or ring-fused pyrazolo[3,4-b] pyridine derivatives, possessing an optionally substituted cycloalkyl, phenyl or heteroaryl substituent on the pyrazole nitrogen atom adjacent the pyridine nucleus, and an optionally substituted cycloalkyl-alkoxy, aryl-alkoxy or heteroaryl-alkoxy substituent on the carbon atom adjacent the pyridine ring nitrogen atom, are selective ligands for GABA$_A$ receptors, in particular having high affinity for the β2 and/or β3 subunit thereof, and are accordingly of benefit in the treatment and/or prevention of adverse neurological disorders, including anxiety and convulsions.

9 Claims, No Drawings

PYRAZOLO-PYRIDINE DERIVATIVES AS LIGANDS FOR GABA RECEPTORS

CROSS REFERENCE TO RELATED APPLICATIONS

This application is a U.S. National Phase application under 35 U.S.C. §371 of PCT Application No. PCT/GB00/04652, filed Dec. 5, 2000, which claims priority under 35 U.S.C. §119 from GB Application No. 9929685.7, filed Dec. 15, 1999.

The present invention relates to a class of substituted pyrazolo-pyridine derivatives and to their use in therapy. More particularly, this invention is concerned with substituted and/or ring-fused pyrazolo[3,4-b]pyridine derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha1\beta2\gamma2$, $\alpha2\beta2/3\gamma2$, $\alpha3\beta\gamma2/3$, $\alpha2\beta\gamma1$, $\alpha5\beta3\gamma2/3$, $\alpha6\beta2$, $\alpha6\beta\delta$ and $\alpha4\beta\delta$. Subtype assemblies containing an $\alpha1$ subunit are present in most areas of the brain and are thought to account for over 40% of $GABA_A$ receptors in the rat. Subtype assemblies containing $\alpha2$ and $\alpha3$ subunits respectively are thought to account for about 25% and 17% of $GABA_A$ receptors in the rat. Subtype assemblies containing an $\alpha5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha1$ subunit in combination with a $\beta$ subunit and $\gamma2$. This is the most abundant $GABA_A$ receptor subtype, and is believed to represent almost half of all $GABA_A$ receptors in the brain.

Two other major populations are the $\alpha2\beta\gamma2$ and $\alpha3\beta\gamma2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha5$-containing subtype assemblies. The physiological role of these subtypes has hitherto been unclear because no sufficiently selective agonists or antagonists were known.

It is now believed that agents acting as BZ agonists at $\alpha1\beta\gamma2$, $\alpha2\beta\gamma2$ or $\alpha3\beta\gamma2$ subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The al-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha1$ subunit. Accordingly, it is considered that $GABA_A$ receptor agonists which interact more favourably with the $\alpha2$ and/or $\alpha3$ subunit than with $\alpha1$ will be effective in the treatment of anxiety with a reduced propensity to cause sedation. Also, agents which are antagonists or inverse agonists at $\alpha1$ might be employed to reverse sedation or hypnosis caused by $\alpha1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

EP-A-0005745 describes inter alia a series of pyrazolo[3,4-c]isoquinoline derivatives which are stated to have activity inter alia as anti-anxiety agents. However, there is no disclosure nor any suggestion in that publication of replacing the benzo moiety of the pyrazolo-isoquinoline ring system with any other functionality, or of varying the substitution around the ring so as to arrive at compounds resembling those provided by the present invention.

The present invention provides a class of pyrazolo-pyridine derivatives which possess desirable binding properties at various $GABA_A$ receptor subtypes. The compounds in accordance with the present invention have good affinity as ligands for the α2 and/or α3 subunit of the human GABA$_A$ receptor. The compounds of this invention may interact more favourably with the α2 and/or α3 subunit than with the al subunit. Desirably, the compounds of the invention will exhibit functional selectivity in terms of a selective efficacy for the α2 and/or α3 subunit relative to the α1 subunit.

The compounds of the present invention are GABA$_A$ receptor subtype ligands having a binding affinity ($K_i$) for the α2 and/or α3 subunit, as measured in the assay described hereinbelow, of 100 nM or less, typically of 50 nM or less, suitably of 20 nM or less, and ideally of 10 nM or less. The compounds in accordance with this invention may possess at least a 2-fold, suitably at least a 5-fold, and advantageously at least a 10-fold, selective affinity for the α2 and/or α3 subunit relative to the al subunit. However, compounds which are not selective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof:

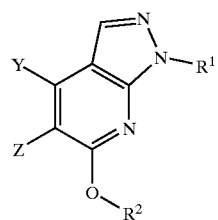

(I)

wherein
Y represents hydrogen, $C_{1-6}$ alkyl, amino, $C_{1-6}$ alkylamino or di($C_{1-6}$)alkylamino; and
Z represents hydrogen, $C_{1-6}$ alkyl, $C_{3-7}$ cycloalkyl, $C_{4-7}$ cycloalkenyl, $C_{6-8}$ bicycloalkyl, aryl, $C_{3-7}$ heterocycloalkyl, heteroaryl, $C_{2-7}$ alkoxycarbonyl or di($C_{1-6}$)alkylamino, any of which groups may be optionally substituted, with the proviso that Y and Z are not both simultaneously hydrogen; or
Y and Z are taken together with the two intervening carbon atoms to form a ring selected from $C_{5-9}$ cycloalkenyl, $C_{6-10}$ bicycloalkenyl, tetrahydropyridinyl, pyridinyl and phenyl, any of which rings may be optionally benzo-fused and/or substituted;
$R^1$ represents $C_{3-7}$ cycloalkyl, phenyl, furyl, thienyl or pyridinyl, any of which groups may be optionally substituted; and
$R^2$ represents $C_{3-7}$ cycloalkyl($C_{1-6}$)alkyl, aryl($C_{1-6}$)alkyl or heteroaryl($C_{1-6}$)alkyl, any of which groups may be optionally substituted.

Where Y and Z are taken together with the two intervening carbon atoms to form a ring, the resulting compounds of formula I above incorporate the relevant cycloalkenyl, bicycloalkenyl, tetrahydropyridinyl, pyridinyl or phenyl ring fused to the central pyrazolo-pyridine ring system as depicted in formula I.

Where Y and Z are taken together with the two intervening carbon atoms to form a $C_{5-9}$ cycloalkenyl ring, this ring may be a cyclopentenyl, cyclohexenyl, cycloheptenyl, cyclooctenyl or cyclononenyl ring, suitably cyclohexenyl or cycloheptenyl.

Where Y and Z are taken together with the two intervening carbon atoms to form a $C_{6-10}$ bicycloalkenyl ring, this ring may be a bicyclo[2.1.1]hex-2-enyl, bicyclo[2.2.1]hept-2-enyl, bicyclo[2.2.2]oct-2-enyl, bicyclo[3.2.2]non-6-enyl or bicyclo[3.3.2]dec-9-enyl ring, suitably bicyclo[2.2.1]hept-2-enyl, bicyclo[2.2.2]oct-2-enyl or bicyclo[3.2.2]non-6-enyl, and especially bicyclo[2.2.2]oct-2-enyl.

Where Y and Z are taken together with the two intervening carbon atoms to form a ring, this ring may be optionally benzo-fused. By way of illustration, Y and Z taken together with the two intervening carbon atoms may represent a benzo-fused cyclohexenyl ring, whereby the resulting ring is dihydronaphthyl.

The groups Y, Z, $R^1$ and $R^2$ may be unsubstituted, or substituted by one or more, suitably by one or two, substituents. In general, the groups Y, Z, $R^1$ and $R^2$ will be unsubstituted or monosubstituted. Examples of optional substituents on the groups Y, Z, $R^1$ and $R^2$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$ alkoxy, $C_{3-7}$ cycloalkyl($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl($C_{1-6}$)alkyl. Specific substituents include $C_{1-6}$ alkyl, halogen and $C_{1-6}$ alkoxy, particularly methyl, ethyl, n-propyl, fluoro or methoxy, and especially methyl, ethyl or fluoro.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, tert-butyl, 1,1-dimethylpropyl and 2,2-dimethylpropyl. Derived expressions such as "$C_{1-6}$ alkoxy" are to be construed accordingly.

Typical $C_{3-7}$ cycloalkyl groups include cyclopropyl, cyclobutyl, cyclopentyl and cyclohexyl.

The expression "$C_{3-7}$ cycloalkyl($C_{1-6}$)alkyl" as used herein includes cyclopropylmethyl, cyclobutylmethyl, cyclopentylmethyl and cyclohexylmethyl.

Typical $C_{4-7}$ cycloalkenyl groups include cyclobutenyl, cyclopentenyl and cyclohexenyl.

Typical aryl groups include phenyl and naphthyl, preferably phenyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thiemylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitably, Y represents hydrogen, methyl or amino, especially hydrogen. In one embodiment, Y represents amino and Z represents hydrogen. In another embodiment, Y represents hydrogen and Z is other than hydrogen.

Representative values for the substituent Z include methyl, ethyl, isopropyl, tert-butyl, 1,1-dimethylpropyl, 2,2-dimethylpropyl, cyclopropyl, methyl-cyclopropyl, cyclobutyl, methyl-cyclobutyl, cyclopentyl, methyl-cyclopentyl, cyclohexyl, cyclobutenyl, bicyclo[2.1 1]hex-1-yl, bicyclo[2.2.1]heptan-1-yl, phenyl, fluorophenyl, pyrrolidinyl, methyl-pyrrolidinyl, piperidinyl, morpholinyl, thiomorpholinyl, pyridinyl, furyl, thienyl, chloro-thienyl, methoxycarbonyl and diethylamino.

Particular values of Z include tert-butyl, 2,2-dimethylpropyl, cyclopropyl, cyclobutyl, cyclopentyl, phenyl, 2-fluorophenyl, 3-fluorophenyl, 4-fluorophenyl, 2-pyridinyl, 3-pyridinyl, 4-pyridinyl, 2-furyl, 3-furyl, 2-thienyl, 3-thienyl and diethylamino.

A specific value of Z is tert-butyl.

In a particular embodiment, the substituent Z represents $C_{3-7}$ cycloalkyl, either unsubstituted or substituted by $C_{1-6}$ alkyl, especially methyl. Favourably, Z may represent cyclobutyl.

When Y and Z are taken together with the two intervening carbon atoms to form a ring, representative compounds according to the invention include those of structure IA to IL:

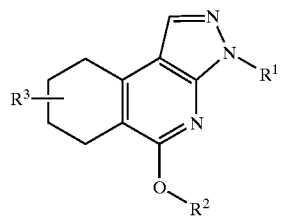

(1A)

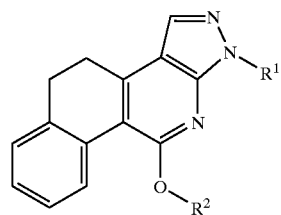

(1B)

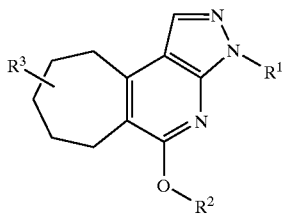

(1C)

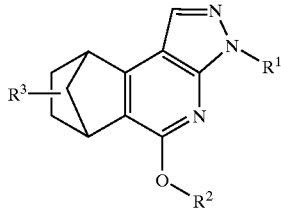

(1D)

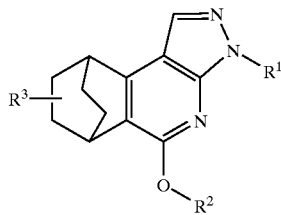

(1E)

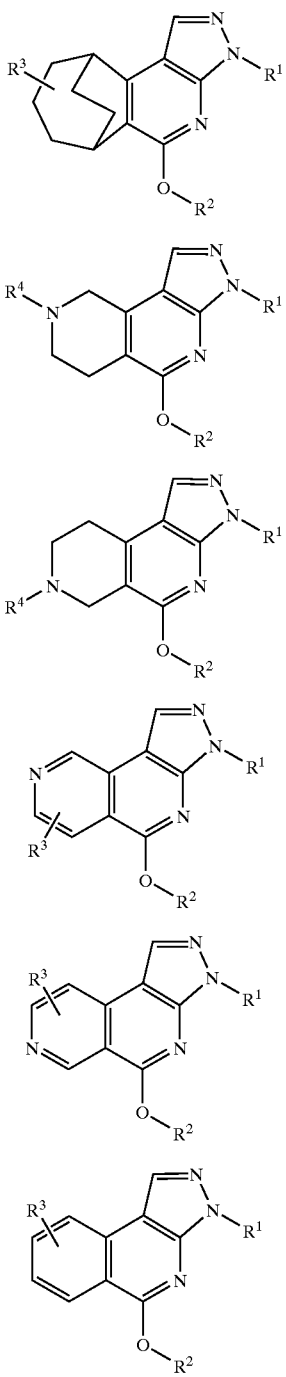

wherein $R^1$ and $R^2$ are as defined above;

$R^3$ represents hydrogen, $C_{1-6}$ alkyl, aryl($C_{1-6}$)alkyl, halogen, cyano, hydroxy, hydroxymethyl or $C_{1-6}$ alkoxy; and $R^4$ represents hydrogen or $C_{1-6}$ alkyl.

Suitably, $R^3$ represents hydrogen or $C_{1-6}$ alkyl, especially hydrogen or methyl.

Suitably, $R^4$ represents hydrogen or methyl.

Favoured ring-fused pyrazolo-pyridine derivatives according to the present invention include the compounds represented by formula IL as depicted above.

Examples of typical optional substituents on the group $R^1$ include methyl, fluoro and methoxy, especially fluoro.

Illustrative values of $R^1$ include cyclopropyl, phenyl, methylphenyl, fluorophenyl, difluorophenyl, trifluorophenyl, methoxyphenyl, (fluoro)(methoxy)phenyl, furyl, thienyl, methyl-thienyl and pyridinyl. In particular, $R^1$ may represent phenyl, fluorophenyl or difluorophenyl. More particularly, $R^2$ may represent unsubstituted or monosubstituted phenyl. Most particularly, $R^1$ represents phenyl or fluorophenyl, especially phenyl.

Suitably, $R^2$ represents aryl($C_{1-6}$)alkyl or heteroaryl($C_{1-6}$)alkyl, either of which groups may be optionally substituted. More particularly, $R^2$ may represent optionally substituted heteroaryl($C_{1-6}$)alkyl.

Suitable values for the substituent $R^2$ in the compounds according to the invention include cyclohexylmethyl, benzyl, pyrazolylmethyl, isoxazolylmethyl, thiazolylmethyl, thiazolylethyl, imidazolylmethyl, benzimidazolylmethyl, oxadiazolylmethyl, triazolylmethyl, tetrazolylmethyl, pyridinylmethyl, pyridazinylmethyl, pyrimidinylmethyl, pyrazinylmethyl, quinolinylmethyl, isoquinolinylmethyl and quinoxalinylmethyl, any of which groups may be optionally substituted by one or more substituents.

Suitably, $R^2$ represents an optionally substituted triazolylmethyl or pyridinylmethyl group. More particularly, $R^2$ represents an optionally substituted triazolylmethyl group.

Examples of suitable optional substituents on the group $R^2$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxymethyl, $C_{1-6}$ alkoxy, $C_{3-7}$ cycloalkyl($C_{1-6}$)alkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl and di($C_{1-6}$)alkylmorpholinyl($C_{1-6}$)alkyl, especially $C_{1-6}$ alkyl.

Specific illustrations of particular substituents on the group $R^2$ include methyl, ethyl, n-propyl, benzyl, pyridinylmethyl, chloro, chloromethyl, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl, morpholinylmethyl and dimethylmorpholinylmethyl.

Typical substituents on $R^2$ include methyl, ethyl and it-propyl, especially methyl or ethyl.

Representative values of $R^2$ include hydroxymethyl-cyclohexylmethyl, cyanobenzyl, hydroxymethyl-benzyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl, methyl-imidazolylmethyl, ethyl-imidazolylmethyl, benzyl-imidazolylmethyl, benzimidazolylmethyl, methyl-oxadiazolylmethyl, triazolylmethyl, methyl-triazolylmethyl, ethyl-triazolylmethyl, propyl-triazolylmethyl, benzyl-triazolylmethyl, pyridinylmethyl-triazolylmethyl, cyanomethyl-triazolylmethyl, dimethylaminomethyl-triazolylmethyl, aminoethyl-triazolylmethyl, dimethylaminoethyl-triazolylmethyl, dimethylaminocarbonylmethyl-triazolylmethyl, N-methylpiperidinyl-triazolylmethyl, pyrrolidinylethyl-triazolylmethyl, piperazinylethyl-triazolylmethyl, morpholinylethyl-triazolylmethyl, methyl-tetrazolylmethyl, pyridinylmethyl, methyl-pyridinylmethyl, dimethyl-pyridinylmethyl, ethoxy-pyridinylmethyl, cyclopropylmethoxy-pyridinylmethyl, pyridazinylmethyl, chloro-pyridazinylmethyl, pyrimidinylmethyl, pyrazinylmethyl, quinolinylmethyl, isoquinolinylmethyl and quinoxalinylmethyl.

Specific values of $R^2$ include methyl-triazolylmethyl, ethyl-triazolylmethyl, propyl-triazolylmethyl and pyridinylmethyl. One favoured value of $R^2$ is methyl-triazolylmethyl. Another favoured value of $R^2$ is ethyl-triazolylmethyl.

A particular sub-class of compounds according to the invention is represented by the compounds of formula IIA, and salts and prodrugs thereof:

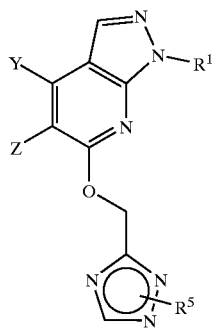

(IIA)

wherein

Y, Z and $R^1$ are as defined with reference to formula I above; and $R^5$ represents hydrogen, methyl, ethyl or n-propyl.

Typically, $R^5$ represents methyl, ethyl or n-propyl. Suitably, $R^5$ represents methyl or ethyl. In one embodiment, $R^5$ is methyl. In another embodiment, $R^5$ is ethyl.

A particular subset of the compounds of formula IIA above is represented by the compounds of formula IIB, and pharmaceutically acceptable salts thereof:

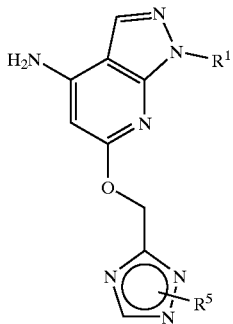

(IIB)

wherein $R^1$ is as defined with reference to formula I above; and $R^5$ is as defined with reference to formula IIA above.

Another subset of the compounds of formula IIA above is represented by the compounds of formula IIC, and pharmaceutically acceptable salts thereof:

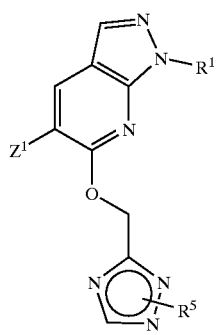

(IIC)

wherein $R^1$ is as defined with reference to formula I above;

$R^5$ is as defined with reference to formula IIA above; and $Z^1$ represents $C_{1-6}$ alkyl or $C_{3-7}$ cycloalkyl.

Selected values for the substituent $Z^1$ include methyl, tert-butyl and cyclobutyl. In one embodiment, $Z^1$ is methyl. In another embodiment, $Z^1$ is tert-butyl.

A further subset of the compounds of formula IIA above is represented by the compounds of formula IID, and pharmaceutically acceptable salts thereof:

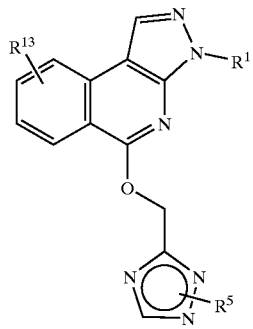

(IID)

wherein $R^1$ is as defined with reference to formula I above;

$R^5$ is as defined with reference to formula IIA above; and $R^{13}$ represents hydrogen or halogen.

Particular values of $R^{13}$ include hydrogen and fluoro, especially hydrogen.

Specific compounds within the scope of the present invention include:

5-(2-methyl-2H-[1,2,4]triazol-3-ylmethoxy)-3-phenyl-3H-pyrazolo[3,4-c]isoquinoline;

5-(2-ethyl-2H-[1,2,4]triazol-3-ylmethoxy)-3-phenyl-3H-pyrazolo [3,4-c]isoquinoline;

5-(1,1-dimethylethyl)-6-(2-methyl-2H-[1,2,4]triazol-3-ylmethoxy)-1-phenyl-1H-pyrazolo[3,4-b]pyridine;

5-(1,1-dimethylethyl)-6-(2-ethyl-2H-[1,2,4]triazol-3-ylmethoxy)-1-phenyl-1H-pyrazolo[3,4-b]pyridine;

5-methyl-6-(2-methyl-2H-[1,2,4]triazol-3-ylmethoxy)-1-phenyl-1H-pyrazolo[3,4-b]pyridine;

6-(2-methyl-2H-[1,2,4]triazol-3-ylmethoxy)-1-phenyl-1H-pyrazolo[3,4-b]pyridin-4-ylamine;

and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the compounds of the invention is ideally 10 nM or less, preferably 2 nM or less, and more preferably 1 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor.

Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I as defined above may be prepared by a process which comprises reacting a compound of formula III with a compound of formula IV:

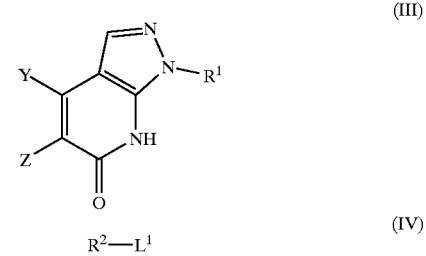

wherein Y, Z, $R^1$ and $R^2$ are as defined above, and $L^1$ represents a suitable leaving group.

The leaving group $L^1$ is typically a halogen atom, especially chloro.

The reaction between compounds III and IV is conveniently effected by stirring the reactants at an elevated temperature in a suitable solvent, in the presence of a base. Typically, the solvent is N,N-dimethylformamide, the base is cesium carbonate, and the reaction is performed at a temperature in the region of 60° C.

The intermediates of formula III above may be prepared by reacting a compound of formula V with a compound of formula VIA or VIB:

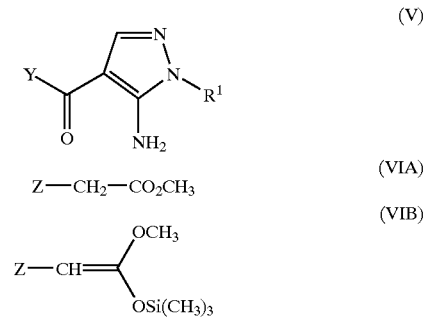

wherein Y, Z and $R^1$ are as defined above.

The reaction between compound V and compound VIA is conveniently effected under basic conditions in a suitable solvent, for example sodium methoxide in methanol.

The reaction between compound V and compound VIB is conveniently effected in the presence of a Lewis acid catalyst, e.g. boron trifluoride etherate, typically in an inert solvent such as dichloromethane at a temperature in the region of −78° C.

Under certain circumstances, for example depending upon the nature of the substituents Y, Z and $R^1$, the reaction between compound V and compound VIA or VIB may give rise to the uncyclized product of formula VIIA and/or VIIB:

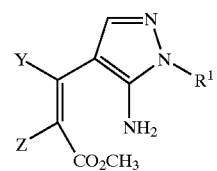

(VIIA)

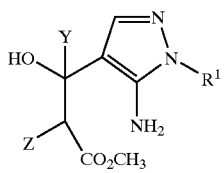

(VIIB)

wherein Y, Z and $R^1$ are as defined above. It will generally be possible to convert compound VIIA and/or VIIB into the desired cyclized product of formula III by treatment with a strong base such a potassium bis(trimethylsilyl)amide, typically in an inert solvent such as tetrahydrofuran at ambient temperature.

In an alternative approach, the intermediates of formula III above may be prepared by reacting a compound of formula VIII with a compound of formula IX:

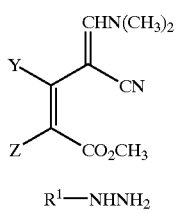

(VIII)

$R^1$—$NHNH_2$ (IX)

wherein Y, Z and $R^1$ are as defined above.

The reaction is conveniently effected at an elevated temperature which may be in the region of 60° C., in the presence of a strong base such as sodium hydride.

The intermediates of formula VIII may be prepared by reacting the corresponding compound of formula X:

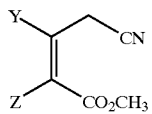

(X)

wherein Y and Z are as defined above; with N,N-dimethylformamide dimethyl acetal.

The reaction is conveniently effected by stirring the reactants at an elevated temperature, which may be in the region of 80° C.

In another procedure, the compounds of formula I as defined above may be prepared by a process which comprises reacting a compound of formula XI with a compound of formula XII:

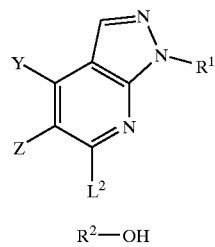

(XI)

$R^2$—OH (XII)

wherein Y, Z, $R^1$ and $R^2$ are as defined above, and $L^2$ represents a suitable leaving group.

The leaving group $L^2$ is suitably a halogen atom, typically chloro.

The reaction between compounds XI and XII is conveniently effected by stirring the reactants in a suitable solvent, typically N,N-dimethylformamide, in the presence of a strong base such as sodium hydride.

In a further procedure, the compounds of formula I as defined above wherein Z represents alkyl, cycloalkyl, aryl or heteroaryl may be prepared by a process which comprises reacting a compound of formula XIII with a compound of formula XIV:

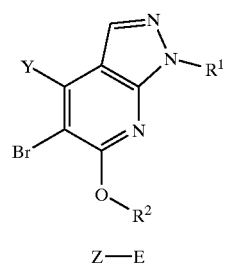

(XIII)

Z—E (XIV)

wherein Y, Z, $R^1$ and $R^2$ are as defined above, and E represents the residue of an organometallic reagent, or E represents —$B(OH)_2$; in the presence of a transition metal catalyst.

Where Z represents alkyl, the reagent of formula XIV is suitably a tetraalkyltin reagent $Z_4Sn$, e.g. tetramethyltin, in which case the transition metal catalyst of use in the reaction between compounds XIII and XIV is ideally dichlorobis(tri-o-tolylphosphine)palladium(II), and the reaction is conveniently effected in a solvent such as N,N-dimethylacetamide, typically in a sealed tube at a temperature in the region of 90° C.

Alternatively, where Z represents alkyl or cycloalkyl, the moiety E may suitably represent the residue of an organozinc reagent, in which case the intermediate XIV is suitably prepared by reacting an alkyl or cycloalkyl halide, e.g. neopentyl iodide or cyclobutyl iodide, with zinc dust, typically in the presence of 1,2-dibromoethane and a solvent such as N,N-dimethylformamide. In this instance, the transition metal catalyst of use in the reaction betwen compounds XIII and XIV is ideally tris(dibenzylideneacetone)dipalladium(0), and the reaction is conveniently effected in the presence of tri-2-furylphosphine and a solvent such as N,N-dimethylformamide.

Where Z represents aryl or heteroaryl, the moiety E suitably represents —$Sn(Alk)3$ in which Alk represents $C_{1-6}$ alkyl, typically n-butyl. In this instance, the transition metal catalyst of use in the reaction between compounds XIII and XIV is ideally tetrakis(triphenylphosphine)-palladium(0), and the reaction is conveniently effected in a solvent such as N,N-dimethylformamide, typically with heating, e.g. to a temperature in the region of 100° C.

Alternatively, where Z represents aryl or heteroaryl, the moiety E may suitably represent —B(OH)$_2$, in which case the transition metal catalyst of use in the reaction between compounds XIII and XIV is ideally tetrakis(triphenylphosphine)palladium(0), and the reaction is conveniently effected in a solvent such as N,N-dimethylformamide, usually with heating, e.g. to a temperature in the region of 100° C., typically in the presence of cesium chloride.

The compounds of formula XIII above may suitably be prepared by reacting a compound of formula IV as defined above with a compound of formula XV:

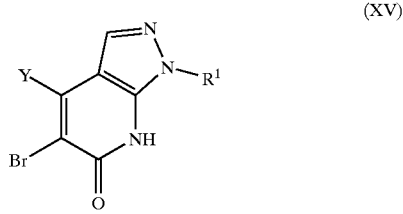

(XV)

wherein Y and R$^1$ are as defined above; under conditions analogous to those described above for the reaction between compounds III and IV.

The compounds of formula XV above may be prepared from the compounds of formula XVI:

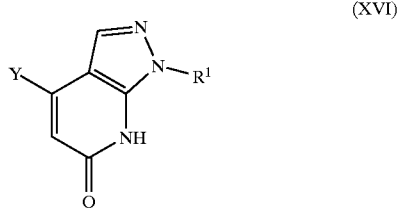

(XVI)

wherein Y and R$^1$ are as defined above; by treatment with bromine, typically in the presence of glacial acetic acid.

The intermediates of formula III above wherein Y is amino and Z is hydrogen may be prepared by reacting a compound of formula XVII:

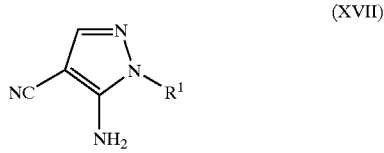

(XVII)

wherein R$^1$ is as defined above; with diethyl malonate; followed by saponification and decarboxylation of the intermediate of formula III wherein Y is amino and Z is ethoxycarbonyl thereby obtained.

The reaction between compound XVII and diethyl malonate is conveniently effected by treatment with sodium ethoxide in ethanol, suitably at reflux.

The subsequent saponification/decarboxylation reaction is conveniently effected by refluxing in aqueous sodium hydroxide solution, followed by neutralization with a mineral acid, e.g. hydrochloric acid.

Where they are not commercially available, the starting materials of formula IV, V, VIA, VIB, IX, X, XI, XII, XIV, XVI and XVII may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I initially obtained wherein R$^2$ is unsubstituted may be converted into a corresponding compound wherein R$^2$ is substituted, typically by standard alkylation procedures, for example by treatment with a haloalkyl derivative in the presence of sodium hydride and N,N-dimethylformamide, or with a hydroxyalkyl derivative in the presence of triphenylphosphine and diethyl azodicarboxylate. Furthermore, a compound of formula I initially obtained wherein the R$^2$ substituent is substituted by a halogen atom, e.g. chloro, may be converted into the corresponding compound wherein the R$^2$ substituent is substituted by a di(C$_{1-6}$)alkylamino moiety by treatment with the appropriate di(C$_{1-6}$)alkylamine, typically with heating in a solvent such as 1,4-dioxane in a sealed tube.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human GABA$_A$ receptors containing the α2 or α3 subunit stably expressed in Ltk$^-$ cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for β1βγ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 subunit of the human GABA$_A$ receptor of 100 nM or less.

EXAMPLE 1

5-(2-Methyl-2H-[1,2,4]triazol-3-ylmethoxy)-3-phenyl-3H-pyrazolo[3,4-c]isoquinoline (a) N N-Dimethyl-2-cyano-2-(2-methoxycarbonylphenyl) ethenylamine A solution of 2-(methoxycarbonyl)phenylacetonitrile (1.0 g, 5.71 mmol) in N,N-dimethylformamide dimethyl acetal (10 ml, 75 mmol) was stirred at 80° C. under nitrogen for 18 h. The mixture was cooled, diluted with ethyl acetate (100 ml) and washed sequentially with water (100 ml) and brine (50 ml). The organic layer was dried (Na$_2$SO$_4$), filtered and concentrated. Flash column chromatography on silica, eluting with 40% ethyl acetate:hexane, gave the title compound (0.43 g, 33%) as colourless needles. δ$_H$ (400 MHz; CDCl$_3$) 3.21 (6H, s), 3.92 (3H, s), 6.57 (1H, s), 7.23–7.28 (2H, m), 7.41 (1H, ddd, J=7, 7 and 1), 7.73 (1H, dd, J=7 and 1); m/z (ES+) 230 (M+H$^+$).

(b) 3,4-Dihydro-3-phenyl-5H-pyrazolo[3,4-c]isoquinolin-5-one

Sodium hydride (0.25 g, 55% in oil, 5.7 mmol) was added to a stirred solution of the preceding product (1.19 g, 5.17 mmol) and phenylhydrazine (0.56 ml, 5.7 mmol) in dry N,N-dimethylformamide (10 ml) at room temperature under nitrogen. The deep purple solution was stirred at room temperature for 1 h, then at 60° C. for 18 h. The solution was poured into water (100 ml) and acidified with aqueous citric acid (1M, 50 ml). The resulting precipitated solid was collected and the aqueous filtrate was extracted with dichloromethane (100 ml). The solid and organic extract were combined, dried (Na$_2$SO$_4$), filtered and concentrated. Trituration and washing with diethyl ether (50 ml) gave 3,4-dihydro-3-phenyl-5H-pyrazolo[3,4-c]isoquinolin-5-one (0.23 g, 17%) as a white powder, m.p. 275 –277° C. δ$_H$ (400 MHz; DMSO+CF$_3$CO$_2$H) 7.43–7.51 (2H, m), 7.57 (2H, dd, J=8 and 8), 7.79–7.83 (3H, m), 8.12 (1H, d, J=8), 8.25 (1H, d, J=8), 8.48 (1H, s); m/z (ES+) 261 (M+H$^+$).

(c) 5-(2-Methyl-2H-[1,2,4]triazol-3-ylmethoxy)-3-phenyl-3H-pyrazolo[3,4-c]isoquinoline A mixture of 3,4-dihydro-3-phenyl-5H-pyrazolo[3,4-c]isoquinolin-5-one (0.10 g, 0.38 mmol), 3-chloromethyl-2-methyl-2H-[1,2,4]triazole hydrochloride (0.10 g, 0.57 mmol) and cesium carbonate (0.37 g, 1.14 mmol) in dry DMF (2 ml) was stirred at 60° C. under nitrogen for 3 h. Water (30 ml) was added and the mixture was filtered. The solids were washed with diethyl ether (5 ml) and dried in vacuo to give the title compound (0.10 g, 74%) as an off-white powder, m.p. 149–151° C. Found: C, 66.19; H, 4.46; N, 23.71. C$_{20}$H$_{16}$N$_6$O.0.25(H$_2$O) requires C, 66.56; H, 4.61; N, 23.29%. δ$_H$ (400 MHz; CDCl$_3$) 3.98 (3H, s), 5.82 (2H, s), 7.36 (1H, dd, J=7 and 7), 7.52–7.57 (3H, m), 7.83 (1H, dd, J=7 and 7), 7.94 (1H, s), 8.15–8.20 (3H, m), 8.33 (1H, d, J=8), 8.42 (1H, s); m/z (ES+) 356 (M+H$^+$).

EXAMPLE 2

5-(2-Ethyl-2H-[1,2,4]triazol-3-ylmethoxy)-3-phenyl-3H-pyrazolo[3,4-c]isoquinoline Prepared as for Example 1, step c), using 3-chloromethyl-2 -ethyl-2H-[1,2,4]triazole hydrochloride (0.10 g, 0.55 mmol) and 3,4-dihydro-3-phenyl-5H-pyrazolo [3,4-c]isoquinolin-5-one (0.095 g, 0.36 mmol) to give the title compound (0.102 g, 76%) as an off-white powder, m.p. 147–148° C. Found: C, 66.49; H, 4.83; N, 22.16. C$_{21}$H$_{18}$N$_6$O.0.5(H$_2$O) requires C, 66.48; H, 5.05; N, 22.15%. δ$_H$ (400 MHz; CDCl$_3$) 1.47 (3H, t, J=7), 4.30 (2H, q, J=7), 5.82 (2H, s), 7.36 (1H, dd, J=8 and 7), 7.51–7.58 (3H, m), 7.83 (1H, dd, J=8 and 7), 7.96 (1H, s), 8.16 (1H, d, J=8), 8.22 (2H, d, J=8), 8.30 (1H, d, J=8), 8.42 (1H, s); m/z (ES+) 371 (M+H$^+$).

EXAMPLE 3

5-(1,1-Dimethylethyl)-6-(2-methyl-2H-[1,2,4]triazol-3-ylmethoxy)-1-phenyl-1H-pyrazolo[3,4-b]pyridine (a) 1,7-Dihydro-5-(1 1-dimethylethyl)-1-phenylpyrazolo [3.4-b]pyridin-6-one To a solution of 5-amino-1-phenyl-1H-pyrazole-4-carboxaldehyde (prepared as described in Bull. Soc. Chim. Belg., 1988, 97, 85–86) (148 mg, 0.79 mmol) in dichloromethane (6 ml) at −78° C. under nitrogen was added a solution of (1-methoxy-3,3-dimethylbut-1-enyloxy) trimethylsilane (J. Org. Chem., 1991, 56, 4737–4741; 0.21 g, 1.04 mmol) in dichloromethane (1.5 ml). Boron trifluoride diethyl etherate (0.10 ml, 0.79 mmol) was added dropwise. After 1 h, a second portion of (1-methoxy-3,3-dimethylbut-1-enyloxy)trimethylsilane (0.44 g, 2.17 mmol) was added as a solution in dichloromethane (1.5 ml). The mixture was stirred for a further 1.5 h and then quenched by addition of saturated aqueous sodium hydrogencarbonate solution. The mixture was diluted with dichloromethane and the layers separated. The aqueous phase was extracted a second time with dichloromethane and then the combined organic extracts were dried (Na$_2$SO$_4$) and concentrated. The product was semi-purified by chromatography on silica eluting with 1% methanol in dichloromethane to give 175 mg of material.

To a solution of the semi-crude product (90 mg) in tetrahydrofuran (5 ml) under nitrogen was added dropwise a solution of potassium bis(trimethylsilyl)amide in toluene (1.1 ml of a 0.5M solution, 0.55 mmol). The resulting mixture was stirred under nitrogen for 17 h and then partitioned between diethyl ether and water. The layers were separated and the aqueous phase extracted a second time with diethyl ether. The combined organic extracts were dried (Na$_2$SO$_4$), and concentrated in vacuo. The product was purified by chromatography on silica using gradient elution with dichloromethane followed by 1% methanol in dichloromethane. 1,7-Dihydro-5-(1,1-dimethylethyl)-1-phenylpyrazolo[3,4-b]pyridin-6-one was obtained as a white solid (28 mg, 26% over 2 steps). δ$_H$ (400 MHz; CDCl$_3$) 1.31 (9H, s), 7.30–7.33 (1H, m), 7.41–7.45 (2H, m), 7.62–7.64 (2H, m), 7.69 (1H, s), 7.81 (1H, s), 10.85 (1H, br s); m/z (ES+) 268 (M+H$^+$).

(b) 5-(1,1-Dimethylethyl)-6-(2-methyl-2H-[1,2,4]triazol-3-ylmethoxy)-1-phenyl-1H-Pyrazolo[3,4-b]pyridine To a solution of 1,7-dihydro-5-(1,1-dimethylethyl)-1-phenylpyrazolo[3,4-b]pyridin-6-one (26 mg, 0.097 mmol) in dry N,N-dimethylformamide (4 ml) under nitrogen was added cesium carbonate (95 mg, 0.29 mmol) followed by 3-chloromethyl-2-methyl-2H-[1,2,4]triazole hydrochloride (25 mg, 0.15 mmol). The reaction mixture was heated at 60° C. for 17 h. The mixture was then allowed to cool and partitioned between water and diethyl ether. The aqueous phase was extracted a second time with diethyl ether and the combined organic extracts were dried (MgSO$_4$) and concentrated to give the title compound as a white solid (25 mg, 71%), m.p. 143–145° C. $\delta_H$ (400 MHz; CDCl$_3$) 1.40 (9H, s), 3.93 (2H, s), 5.69 (1H, s), 7.29–7.32 (1H, m), 7.49–7.53 (2H, m), 7.93 (1H, s), 7.98 (1H, s), 8.05 (1H, s), 8.19–8.21 (2H, m); m/z (ES+) 363 (M+H$^+$)

EXAMPLE 4

5-(1,1-Dimethylethyl)-6-(2-ethyl-2H-[1,2,4]triazol-3-ylmethoxy)-1-phenyl-1H-pyrazolo[3,4-b]pyridine Prepared as for Example 3, step b), using 3-chloromethyl-2-ethyl-2H-[1,2,4]triazole hydrochloride, m.p. 150–152° C. Found: C, 67.06; H, 6.30; N, 22.18. C$_{21}$H$_{24}$N$_6$O requires C, 67.00; H, 6.43; N, 22.32%. $\delta_H$ (400 MHz; CDCl$_3$) 1.40 (9H, s), 1.44 (3H, t, J=7), 4.26 (2H, q, J=7), 5.69 (2H, s), 7.29–7.33 (1H, m), 7.50–7.54 (2H, m), 7.95 (1H, s), 7.97 (1H, s), 8.05 (1H, s), 8.21 (2H, dd, J=9 and 1); m/z (ES+) 377 (M+H$^+$).

EXAMPLE 5

5-Methyl-6-(2-methyl-2H-[1,2,4]triazol-3-ylmethoxy)-1-phenyl-1H-pyrazolo[3.4-b]pyridine (a) 1,7-Dihydro-1-phenylpyrazolo [3,4-b]pyridin-6-one To a semi-solid mixture of 18-crown-6 (4.31 g, 16 mmol) and THF (30 ml) at −40° C. under nitrogen was added bis(2,2,2-trifluoroethyl)-(methoxycarbonylmethyl) phosphonate (0.69 ml, 3.26 mmol) followed by a solution of potassium bis(trimethylsilyl)amide in toluene (6.52 ml of a 0.5M solution, 3.26 mmol). A solution of 5-amino-1-phenyl-1H-pyrazole-4-carboxaldehyde (0.61 g, 3.26 mmol) in THF (10 ml+5 ml washings) was then added via cannula and the resulting mixture was stirred for 20 h, allowing to warm to room temperature. The reaction mixture was partitioned between saturated aqueous ammonium chloride solution and diethyl ether. The aqueous phase was extracted a second time with diethyl ether, and the combined organic extracts were washed with brine, dried (MgSO$_4$) and concentrated. The crude material was dissolved in THF (20 ml), under nitrogen, and the resulting solution cooled to 0° C. A solution of potassium bis(trimethylsilyl)amide in toluene (13.0 ml of a 0.5M solution, 6.5 mmol) was added dropwise and the reaction mixture was stirred for 17 h during which time it was allowed to warm to room temperature. The reaction mixture was partitioned between saturated aqueous ammonium chloride solution and ethyl acetate. The aqueous phase was extracted a second time with ethyl acetate, and the combined organic extracts were washed sequentially with 0.5M aqueous hydrochloric acid and brine before being dried (MgSO$_4$) and concentrated in vacuo. The crude material was purified by chromatography on silica eluting with 30% ethyl acetate-hexane to give 1,7-dihydro-1-phenylpyrazolo[3,4-b]pyridin-6-one (0.49 g, 71%). $\delta_H$ (400 MHz; CDCl$_3$) 6.50 (1H, d, J=9), 7.29–7.33 (1H, m), 7.42–7.45 (2H, m), 7.71–7.73 (2H, m), 7.85 (1H, d, J=9), 7.91 (1H, s).

(b) 5-Bromo-1,7-dihydro-1-phenylpyrazolo[3,4-b]pyridin-6-one

Bromine (76 μl, 1.47 mmol) was added to a solution of 1-phenyl-1,7-dihydropyrazolo[3,4-b]pyridin-6-one (0.31 g, 1.47 mmol) in acetic acid (7 ml) and the mixture was stirred for 30 min. The suspension was diluted with water, stirred for 10 min and then the precipitate filtered off, washing with water. The product was dried in a desiccator at 40° C. under vacuum for 17 h to give 5-bromo-1,7-dihydro-1-phenylpyrazolo[3,4-b]pyridin-6-one (0.29 g, 68%) as a brown solid. $\delta_H$ (400 MHz; DMSO) 7.32–7.37 (1H, m), 7.52–7.58 (2H, m), 8.12–8.24 (3H, m), 8.50 (1H, s); m/z (ES+) 290 (M+H+), 292 (M+H$^+$).

(c) 5-Bromo-6-(2-methyl-2H-[1,2,4]triazol-3-ylmethoxy)-1-phenyl-1H-pyrazolo[3,4-b]pyridine To a solution of 5-bromo-1,7-dihydro-1-phenylpyrazolo [3,4-b]pyridin-6-one (0.29 g, 1.0 mmol) in DMF (4 ml) under nitrogen was added cesium carbonate (0.98 g, 3.0 mmol) followed by 3-chloromethyl-2-methyl-2H-[1,2,4] triazole hydrochloride (0.25 g, 1.5 mmol). The resulting suspension was heated at 60° C. for 17 h. The mixture was partitioned between ammonium chloride solution (saturated aqueous) and ethyl acetate. The layers were separated and the aqueous phase extracted a second time with ethyl acetate. The combined organic extracts were washed with brine, dried (MgSO$_4$) and concentrated in vacuo to give 5-bromo-6-(2-methyl-2H-[1,2,4]triazol-3-ylmethoxy)-1-phenyl-1H-pyrazolo[3,4-b]pyridine (0.40 g) of adequate purity. $\delta_H$ (400 MHz; CDCl$_3$) 4.04 (3H, s), 5.70 (2H, s), 7.33–7.37 (1H, m), 7.52–7.56 (2H, m), 7.90 (1H, s), 8.06 (1H, s), 8.16–8.19 (2H, m), 8.27 (1H, s); m/z (ES+) 387 (M+H$^+$), 385 (M+H$^+$).

(d) 5-Methyl-6-(2-methyl-2H-[1,2,4]triazol-3-ylmethoxy)-1-phenyl-1H-pyrazolo[3,4-b]pyridine To a de-gassed solution of 5-bromo-6-(2-methyl-2H-[1,2,4]triazol-3-ylmethoxy)-1-phenyl-1H-pyrazolo[3,4-b] pyridine (84 mg, 0.22 mmol) in N,N-dimethylacetamide (2 ml) was added tetramethyltin (60 μl, 0.43 mmol) followed by dichlorobis(tri-ortho-tolylphosphine)palladium(II) (8.6 mg, 0.01 mmol). The reaction mixture was heated at 90° C. in a sealed tube for 20 h. The mixture was allowed to cool, quenched with saturated aqueous ammonium chloride solution and the product extracted into diethyl ether (×3). The combined organic extracts were washed with brine, dried (MgSO$_4$) and concentrated in vacuo. Purification by preparative thin layer chromatography, eluting with 55% ethyl acetate-hexane, afforded the title compound as a white solid (20 mg, 29%), m.p. 145–146° C. $\delta_H$ (400 MHz; CDCl$_3$) 2.32 (3H, s), 3.96 (3H, s), 5.66 (2H, s), 7.31 (1H, t, J=7), 7.50–7.54 (2H, m), 7.82 (1H, s), 7.91 (1H, s), 8.02 (1H, s), 8.19–8.22 (2H, m); m/z (ES+) 321 (M+H$^+$).

EXAMPLE 6

6-(2-Methyl-2H-[1,2,4]triazol-3-ylmethoxy)-1-phenyl-1H-pyrazolo [3,4-b]pyridin-4-ylamine (a) 4-Amino-6.7-dihydro-6-oxo-1-phenyl-1H-pyrazolo [3,4-b]pyridine-5-carboxylic Acid Ethyl Ester Sodium pellets (0.86 g, 37.4 mmol) were added carefully to dry ethanol (40 ml) in a round-bottomed flask with a condenser in place and under nitrogen. The resulting solution of sodium ethoxide was allowed to cool to room temperature before addition of diethyl malonate (4.74 ml, 31.2 mmol). 5-Amino-1-phenylpyrazole-4-carbonitrile (2.30 g, 12.5 mmol) was added portionwise and the mixture heated at reflux for 4 h. The mixture was cooled and the ethanol removed in vacuo. Water (25 ml) was added to the residue and the solid was filtered off, washing with water. 4-Amino-6,7-dihydro-6-oxo-1-phenyl-1H-pyrazolo [3,4-b] pyridine-5-carboxylic acid ethyl ester (1.5 g, 40%) was obtained as a white solid. $\delta_H$ (400 MHz; DMSO) 1.35 (3H, t, J=7), 4.40 (2H, q, J=7), 7.30–7.34 (1H, m), 7.49–7.54 (2H, m), 8.04 (2H, br s), 8.09 (2H, br d, J=8), 8.44 (1H, s), 12.20 (1H, br s).

(b) 4-Amino-1,7-dihydro-1-phenylpyrazolo[3,4-b]pyrdin-6-one

4-Amino-6,7-dihydro-6-oxo-1-phenyl-1H-pyrazolo[3,4-b]pyridine-5-carboxylic acid ethyl ester (0.68 g, 2.28 mmol) was heated at reflux in sodium hydroxide solution (12 ml of a 15 wt. % solution in water). After 6 h, the mixture was allowed to cool to room temperature and was then transferred to a fridge and kept there for 19 h. The white precipitate was filtered off and the filtrate set aside. The solid was dissolved in water and acidified to pH 5 by dropwise addition of concentrated hydrochloric acid. The product was extracted into ethyl acetate (×2) and the combined organic layers washed with brine before being dried (MgSO$_4$) and concentrated. 4-Amino-1,7-dihydro-1-phenylpyrazolo[3,4-b]pyridin-6-one (324 mg, 63%) was obtained as a white solid. The filtrate which had been set aside was acidified to pH 5 and extracted with ethyl acetate (×2). The combined organic extracts were washed with saturated aqueous sodium hydrogencarbonate solution and then brine before being dried (MgSO$_4$) and concentrated. This afforded a second crop of the product (145 mg, total yield 91%), m.p. 223–225° C. $\delta_H$ (400 MHz; DMSO) 5.58 (1H, s), 6.76 (2H, br s), 7.23–7.27 (1H, m), 7.46–7.50 (2H, m), 8.16 (1H, s), 8.21–8.24 (2H; m), 11.16 (1H, br s); m/z (ES+) 227 (M+H$^+$).

(c) 6-(2-Methyl-2H-[1,2,4]triazol-3-ylmethoxy)-1-phenyl-1H-pyrazolo[3,4-b]pyridin-4-ylamine To a solution of 4-amino-1,7-dihydro-1-phenylpyrazolo[3,4-b]pyridin-6-one (0.30 g, 1.33 mmol) in DMF (8 ml) under nitrogen was added cesium carbonate (0.95 g, 2.92 mmol) followed by 3-chloromethyl-2-methyl-2H-[1,2,4] triazole hydrochloride (0.27 g, 1.61 mmol). The resulting suspension was heated at 60° C. for 17 h. The mixture was partitioned between saturated aqueous ammonium chloride solution and ethyl acetate. The layers were separated and the aqueous phase extracted a second time with ethyl acetate. The combined organic extracts were washed with brine, dried (MgSO$_4$) and concentrated in vacuo to give the title compound as a white solid (0.41 g, 96%), m.p. 164–166° C. $\delta_H$ (400 MHz; CDCl$_3$) 3.91 (3H, s), 4.70 (2H, br s), 5.58 (2H, s), 5.89 (1H, s), 7.28–7.31 (1H, m), 7.48–7.52 (2H, m), 7.88 (1H, s), 7.98 (1H, s), 8.15–8.18 (2H, m); m/z (ES+) 322 (M+H$^+$).

What is claimed is:

1. A compound of formula I, or a salt thereof:

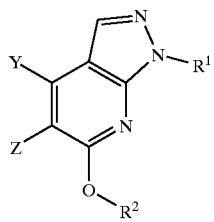

(I)

wherein

Y represents hydrogen, C$_{1-6}$ alkyl, amino, C$_{1-6}$ alkylamino or di(C$_{1-6}$)alkylamino; and Z represents hydrogen, C$_{1-6}$ alkyl, C$_{3-7}$ cycloalkyl, C$_{4-7}$ cycloalkenyl, C$_{6-8}$ bicycloalkyl, aryl, C$_{3-7}$ heterocycloalkyl, heteroaryl, C$_{2-7}$ alkoxycarbonyl or di(C$_{1-6}$)alkylamino, any of which groups may be optionally substituted, with the proviso that Y and Z are not both simultaneously hydrogen; or Y and Z are taken together with the two intervening carbon atoms to form a ring selected from C$_{5-9}$ cycloalkenyl, C$_{6-10}$ bicycloalkenyl, tetrahydropyridinyl, pyridinyl and phenyl, any of which rings may be optionally benzo-fused and/or substituted;

R$^1$ represents C$_{3-7}$ cycloalkyl, phenyl, furyl, thienyl or pyridinyl, any of which groups may be optionally substituted; and R$^2$ represents C$_{3-7}$ cycloalkyl(C$_{1-6}$)alkyl, aryl(C$_{1-6}$)alkyl or heteroaryl(C$_{1-6}$)alkyl, any of which groups may be optionally substituted.

2. A compound as claimed in claim 1 represented by formula IIA, and salts thereof:

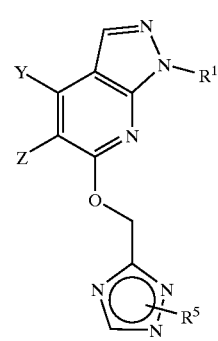

(IIA)

wherein

R$^5$ represents hydrogen, methyl, ethyl or n-propyl.

3. A compound as claimed in claim 2 represented by formula IIB, and pharmaceutically acceptable salts thereof:

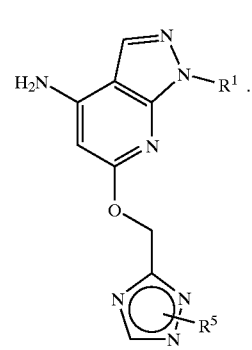

(IIB)

4. A compound as claimed in claim 2 represented by formula IIC, and pharmaceutically acceptable salts thereof:

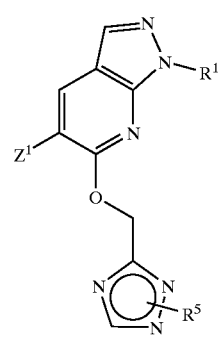

(IIC)

wherein

Z$^1$ represents C$_{1-6}$ alkyl or C$_{3-7}$ cycloalkyl.

5. A compound as claimed in claim 2 represented by formula IID, and pharmaceutically acceptable salts thereof:

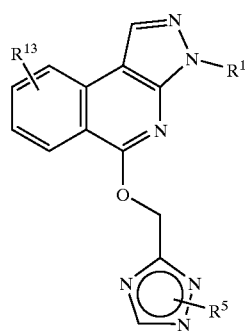

(IID)

wherein
R[13] represents hydrogen or halogen.

6. A compound selected from:
5-(2-methyl-2H-[1,2,4]triazol-3-ylmethoxy)-3-phenyl-3H-pyrazolo[3,4-c]isoquinoline;
5-(2-ethyl-2H-[1,2,4]triazol-3-ylmethoxy)-3-phenyl-3H-pyrazolo[3,4-c]isoquinoline;
5-(1,1-dimethylethyl)-6-(2-methyl-2H-[1,2,4]triazol-3-ylmethoxy)-1-phenyl-1H-pyrazolo[3,4-b]pyridine;
5-(1,1-dimethylethyl)-6-(2-ethyl-2H-[1,2,4]triazol-3-ylmethoxy)-1-phenyl-1H-pyrazolo[3,4-b]pyridine;
5-methyl-6-(2-methyl-2H-[1,2,4]triazol-3-ylmethoxy)-1-phenyl-1H-pyrazolo[3,4-b]pyridine;
6-(2-methyl-2H-[1,2,4]triazol-3-ylmethoxy)-1-phenyl-1H-pyrazolo[3,4-b]pyridin-4-ylamine;
and salts and prodrugs thereof.

7. A pharmaceutical composition comprising a compound of formula I as defined in claim 1 or a pharmaceutically acceptable salt thereof in association with a pharmaceutically acceptable carrier.

8. A method for the treatment or prevention of anxiety which comprises administering to a patient in need of such treatment an effective amount of a compound of formula I as defined in claim 1 or a pharmaceutically acceptable salt thereof.

9. A process for the preparation of a compound of formula I as defined in claim 1, which comprises:

(A) reacting a compound of formula III with a compound of formula IV:

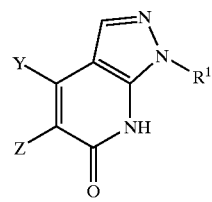

(III)

$R^2\text{—}L^1$ (IV)

wherein Y, Z, $R^1$ and $R^2$ are as defined in claim 1, and $L^1$ represents a suitable leaving group; or (B) reacting a compound of formula XI with a compound of formula XII:

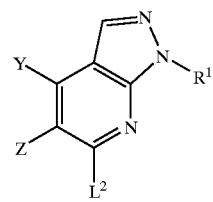

(XI)

$R^2\text{—OH}$ (XII)

wherein Y, Z, $R^1$ and $R^2$ are as defined in claim 1, and $L^2$ represents a suitable leaving group; or (C) reacting a compound of formula XIII with a compound of formula XIV:

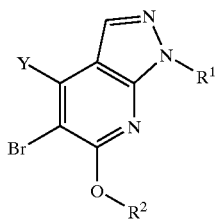

(XIII)

Z—E. (XIV)

wherein Y, Z, $R^1$ and $R^2$ are as defined in claim 1, and E represents the residue of an organometallic reagent, or E represents —B(OH)$_2$; in the presence of a transition metal catalyst; and (D) subsequently, if desired, converting a compound of formula I initially obtained into a further compound of formula I.

* * * * *